United States Patent [19]

Levine

[11] Patent Number: 5,104,377
[45] Date of Patent: Apr. 14, 1992

[54] UTERINE ACCESS DEVICE WITH AUTOMATIC CERVICAL ADJUSTMENT

[75] Inventor: Andy H. Levine, Boston, Mass.

[73] Assignee: C. R. Bard, Inc., Murray Hill, N.J.

[21] Appl. No.: 630,723

[22] Filed: Dec. 20, 1990

Related U.S. Application Data

[63] Continuation of Ser. No. 392,040, Aug. 10, 1989, abandoned.

[51] Int. Cl.⁵ .......................................... A61M 29/00
[52] U.S. Cl. .................................. 604/101; 604/55; 606/193
[58] Field of Search .......................... 604/54–55, 604/93, 96–99, 101, 264; 606/119, 191–193

[56] References Cited

U.S. PATENT DOCUMENTS

| | | | |
|---|---|---|---|
| 2,610,626 | 9/1952 | Edwards | 128/231 |
| 2,687,131 | 8/1954 | Raiche | 128/349 |
| 3,154,077 | 10/1964 | Cannon | 604/101 |
| 3,411,506 | 11/1968 | Velasco | 604/101 |
| 3,848,602 | 11/1974 | Gutnick | 606/193 |
| 4,083,369 | 4/1978 | Sinnreich | 128/276 |
| 4,430,076 | 2/1984 | Harris | 604/96 |
| 4,664,114 | 5/1987 | Ghodsian | 128/344 |
| 4,693,704 | 9/1987 | Ogita | 604/55 |
| 4,696,668 | 9/1987 | Wilcox | 604/101 |
| 4,775,362 | 10/1988 | Kronner | 604/96 |
| 4,976,692 | 12/1990 | Atad | 604/101 |

FOREIGN PATENT DOCUMENTS

| | | |
|---|---|---|
| 0088714 | 9/1983 | European Pat. Off. |
| 0141589 | 5/1985 | European Pat. Off. |
| 0299158 | 1/1989 | European Pat. Off. |
| 0362146 | 4/1990 | European Pat. Off. |

OTHER PUBLICATIONS

Neuman et al., "Continuous Monitoring of Cervical Dilatation During Labor and Measurement of Cervical Compliance in the Human", *Dilatation of the Uterine Cervix Connective Tissue Biology and Clinical Management*, Chap. 16, pp. 233–245, Raven Press, New York, 1980.

*Primary Examiner*—C. Fred Rosenbaum
*Assistant Examiner*—C. Maglione
*Attorney, Agent, or Firm*—Wolf, Greenfield & Sacks

[57] ABSTRACT

A device and method for accessing the uterus to manipulate it or to introduce fluids or other devices into it. The device includes a shaft having a first, expandable distal member which is inserted into the uterus and a second, inflatable proximal member which is inserted partially into the cervical canal. The proximal member automatically adjusts to the length of the cervical canal upon inflation because only the proximal portion of the proximal member which is outside of the cervical canal expands. During use of the device, the distal member is expanded within the uterus and the shaft is withdrawn proximally until the expanded distal device contacts the internal os of the cervix. The proximal member is then inflated proximal to the exterior os of the cervix. The distal portion of the proximal member lies within and is obstructed by the cervical canal. The distal and proximal members thereby cooperate to securely couple the shaft to the uterus by automatically adjusting to the length of the cervical canal.

23 Claims, 2 Drawing Sheets

UTERINE ACCESS DEVICE WITH AUTOMATIC CERVICAL ADJUSTMENT

This application is a continuation of application Ser. No. 07/392,040, filed Aug. 10, 1989, now abandoned.

FIELD OF THE INVENTION

This invention relates to devices for accessing a uterus for manipulation or for introduction of fluids or other devices into the uterus and fallopian tubes, and to techniques for performing the uterine access.

BACKGROUND OF THE INVENTION

There are a number of situations in which it is desirable to examine the uterus and fallopian tubes to evaluate female infertility. In one situation, for example, the patency of the fallopian tubes must be determined. This is usually accomplished by radiographic or laparoscopic examination.

To perform a radiographic evaluation, a radiopaque contrast liquid is injected into the uterus to enable examination under fluoroscopy of the contours of the uterus and the patency of the fallopian tube(s). This procedure is known as hysterosalpingography (HSG). When the contrast media is initially injected into the uterus, the HSG often incorrectly indicates blocked fallopian tubes. Such incorrect results are frequently due to insufficient injection pressure.

It is desirable to pressurize the uterus during injection of the contrast liquid, and a number of presently available devices attempt to do so. It is difficult to establish a seal between the uterus and the vagina, however, and leakage of the contrast liquid is a problem.

The reproductive tract can also be studied using a laparoscope, which is a tubular device inserted through an incision made in the abdomen of the patient rather than being passed through the inside of the reproductive tract. The outside of the reproductive organs and the distal openings of the fallopian tubes near the ovaries can be examined through the laparoscope. Patency of the fallopian tubes is tested by injecting a colored dye into the uterus and observing spillage of the dye through the tubes into the abdominal cavity. Again, present injection devices may not properly seal the uterus and sufficiently high injection pressures may not be attainable. False patency test results may occur.

Particularly during laparoscopic examination, it is desirable to manipulate the uterus to permit observation of different areas of the uterus and surrounding organs. This is commonly accomplished by attempting to engage the cervix, which is the neck of the uterus, with a manipulator device. The device is inserted into the external opening of the cervix, referred to as the external os, and passed through the cervical canal into the uterus. The internal opening of the cervix is known as the internal os. Several conventional manipulator devices have a distal inflatable member which is inflated within the uterus to engage the internal os to prevent the device from pulling out of the uterus. A proximal stop is provided to prevent the device from being inserted further into the uterus.

The length of the cervical canal varies from patient to patient, however, and no one setting is appropriate for all patients. The present manipulator devices are commonly provided with a moveable proximal stop which must be manually adjusted in an attempt to properly seat against the external os. The process of adjusting the device to the different cervical lengths is cumbersome and may involve one or more resettings of the proximal stop to securely engage the cervix. Application of excessive force by the proximal stop may cause discomfort to the patient or undesired withdrawal of the distal member even when it is inflated.

SUMMARY OF THE INVENTION

The uterine access device of the invention has an element which automatically adjusts to the length of the cervical canal. The device has a shaft having a first, expandable distal member which is inserted into the uterus and then expanded. The shaft also carries a second, inflatable proximal member which is inserted partially through the cervical canal. Upon inflation of the proximal member, only the portion which is outside of the cervical canal expands. The inflated portion of the proximal member therefore is automatically positioned against the external os, and the distal and proximal members exert clamping forces toward each other to securely couple the shaft to the cervix. The variable expansion along the length of the proximal member thereby provides automatic adjustment to the actual length of the cervical canal.

The device, once clamped to the cervix, can be used to manipulate the uterus, such as during laporoscopic examination of the reproductive organs, or to introduce fluids or other devices through it into the uterus. In one embodiment, the distal member is an inflatable balloon which is disposed about the shaft. The distal member sealingly engages the internal os of the cervix, and the distal and proximal members exert forces toward each other to seal the device within the cervical canal and block flow of fluid from the uterus along the exterior of the shaft. The shaft or other structure defines first and second lumens which communicate with the distal and proximal members to enable actuation of the members.

In a preferred embodiment, a third lumen is defined in the shaft through which fluids or devices can be introduced into the uterus. Alternatively, such as when the device is used only to manipulate the uterus, only the inflation lumens are defined in the shaft and the shaft is otherwise solid. Preferably, the shaft defines at least two ports through which the second lumen communicates with the proximal member, one of the ports being disposed beneath the distal portion of the proximal member and another port being disposed beneath the proximal portion. The third lumen extends from the proximal end of the shaft to its distal end, and the proximal end of the shaft extends external to the patient to serve as a handle for manipulating the uterus when the device is positioned within the cervical canal. A metal rod may be inserted into the third lumen to further stiffen the shaft.

Preferably the distal end of the shaft is inclined at an angle relative to the remainder of the shaft to facilitate insertion into the cervix and the uterus. The angle may range from 15 to 25 degrees. Further, the distal portion of the proximal member may have a wall thickness less than that of the proximal portion to preferentially induce expansion of the proximal member immediately proximal to the external os of the cervix. A preferred compliant material for the proximal member is latex. The material is sufficiently compliant that, during inflation, substantially all expansion of the proximal member occurs in the proximal portion and expansion of the distal portion is restricted by the cervical canal. Little or no dilatation of the cervical canal occurs.

A preferred technique of using such a device involves inserting the distal end of the shaft through the cervical canal to place the distal member within the uterus, expanding the distal member to increase its diameter beyond that of the cervical canal, and withdrawing the device until the expanded distal member contacts the internal os of the cervix. The proximal member then is inflated proximal to the external os of the cervix. The distal and proximal members thereby cooperate to securely couple the shaft to the uterus by automatically adjusting to the length of the cervical canal.

It is among the objects of the invention to provide a new device and technique for accessing the uterus.

Another object of the invention is to provide an improved device which automatically adjusts to the specific length f the cervical canal.

It is a further object of the invention to provide such a device which reliably seals the uterus to minimize leakage of dye, contrast liquid or other fluids injected into the uterus.

A still further object of the invention is to provide such a device which enables higher injection pressures of fluid into the uterus and fallopian tubes.

A further object of the invention is to provide an improved device and technique for manipulating the uterus by securely and automatically gripping both ends of the cervical canal while minimizing trauma to the reproductive tract.

Yet another object of the invention is to provide an improved introducer device through which other instruments can be passed to access the uterus and the fallopian tubes.

DESCRIPTION OF THE ILLUSTRATIVE EMBODIMENT

A device and method according to this invention for accessing the uterus to manipulate it or to introduce fluids and other devices into it can be accomplished by a shaft having a first, expandable distal member which is inserted into the uterus and expanded. The shaft carries a second, inflatable proximal member which is inserted partially into the cervical canal. Upon inflation of the proximal member, only the portion which is outside of the cervical canal expands, thereby automatically adjusting to the actual length of that cervical canal. Preferably, the shaft is a hollow, elongate tube through which fluids or instruments can be introduced into the uterus and fallopian tubes.

Figures 1, 2:
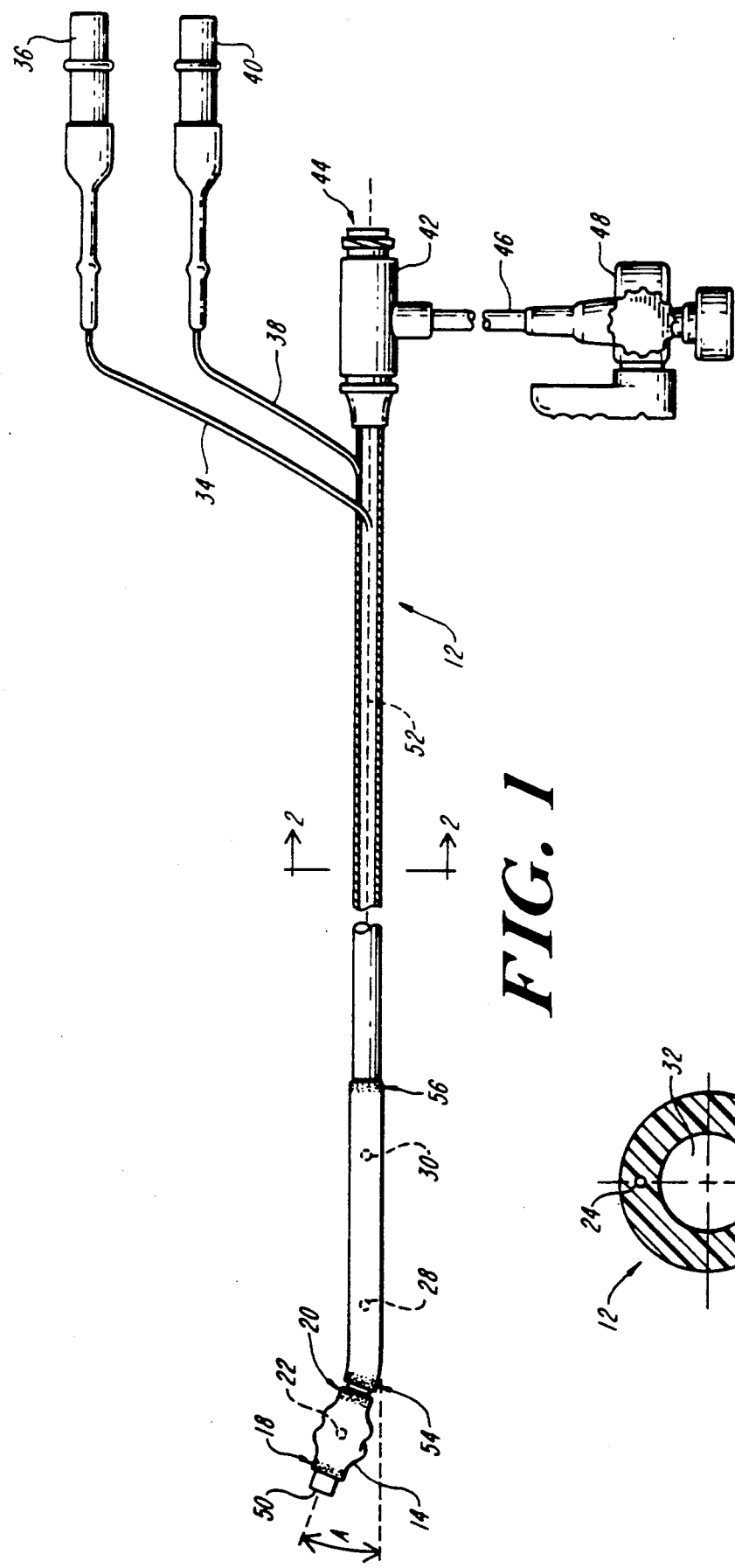
FIG. 1 is a schematic side view of the uterine access device of the invention.
FIG. 2 is a cross-section along lines 2—2 of FIG. 1.

A uterine access device 10 according to this invention is shown in FIG. 1 having shaft 12 on which are disposed a first, expandable distal member 14 and a second, inflatable proximal member 16. In this construction, the distal member 14 is an inflatable balloon formed by a vinyl sleeve which is bonded at a distal region 18 and a proximal region 20 to the shaft 12. The distal member 14 is inflated through a port 22, shown in phantom, which communicates with a lumen 24 which is defined by the shaft 12 as shown in FIG. 2. The shaft 12 also defines a lumen 26 which communicates with ports 28, 30 and a large, central lumen 32 which runs the full length of the shaft 12 and terminates in a distal orifice having the same diameter as the central lumen 32. The lumens 24, 26 are preferably spaced oppositely from each other as shown. The lumen 24 is connected near its proximal end to a tube 34 which terminates in a self sealing air valve 36. Similarly, the lumen 26 is connected near its proximal end with a tube 38 and a air valve 40.

Preferably, the shaft 12 is a vinyl or polycarbonate tube formed by extrusion to have a length of 10.75 inch (27.3 cm), an outer diameter of 0.157 inch (4 mm) and an inner diameter of 0.080 inch 2 mm). Lumens 24, 26 are preferably 0.010 inch (0.25 mm) in diameter. A valve device 42 is connected to the proximal end of the shaft 12 to enable instruments or other devices to be inserted through the lumen 32 while maintaining a seal to prevent the escape of fluids through opening 44 when contrast liquids or other fluids are injected into the uterus. The seal is maintained by a gasket which closes around the device, such as found in U.S. Pat. No. 4,424,833 by Spector et al. The device 42 further includes an injection port accessed through tube 46 and stopcock 48. Dye, contrast liquids, or other fluids can thereby be injected into the central lumen 32 to be discharged through the distal orifice at the distal end 50 of the shaft 12.

The distal end 50 of the shaft is rounded to avoid trauma to the cervical canal and the uterus, and a distal portion of the shaft 12 is preferably inclined relative to the longitudinal axis 52 of the shaft 12. The inclination of the distal portion provides easier location of and insertion into the cervical canal because the cervix and uterus are inclined relative to the vagina. Also, the inclination of the distal portion minimizes trauma to the cervix and uterus. The inclination is represented by angle A which may range from 0°-30° and is preferably 15°-25°. Angle A in this construction is 20 degrees, and the length of the inclined distal portion is 0.6 inch (15.2 mm).

Preferably, the second, proximal balloon 16 is more compliant than the first, distal balloon 14. Rather than vinyl or polyurethane, which is moderately compliant and suitable for the distal balloon 14, the proximal balloon 16 is preferably formed of a latex material. The proximal balloon 16 is of sufficient length so that a distal portion remains within the cervical canal while the remaining proximal portion inflates, as described in more detail below. The proximal balloon 16 is preferably at least 1.5 inch in length, and in this construction is 2.0 inch in length and secured to the shaft 12 by bonds 54, 56 which are each approximately 0.08 inch (2 mm) in length. Both the distal and proximal balloons can be bonded with a cyanoacrylate such as Loctite 495 available from Loctite Corporation. Alternatively, an epoxy such as FDA 2 available from Tra-Con, Inc. can be used. In another construction, the proximal and distal ends of the proximal balloon 16 are wrapped with a suture thread which is tied and/or coated with adhesive to secure the thread about the balloon 16.

It is desirable for the wall thickness of the proximal balloon 16 to increase from the distal bond 54 toward the proximal bond 56 to preferentially induce expansion immediately proximal to the external os. In this construction, the proximal balloon 16 has a wall of 0.010 inch at the distal end ranging proximally to 0.012 inch at the proximal end. This is accomplished during manufacture b dip coating the balloon with a mandrel which is held in a vertical position, thereby allowing gravity to draw slightly more material toward the downward end, which becomes the proximal end of the balloon. By comparison, the distal balloon 14 when fabricated of vinyl has a wall thickness of 0.015 inch and length of 0.5 inch.

Figure 3:
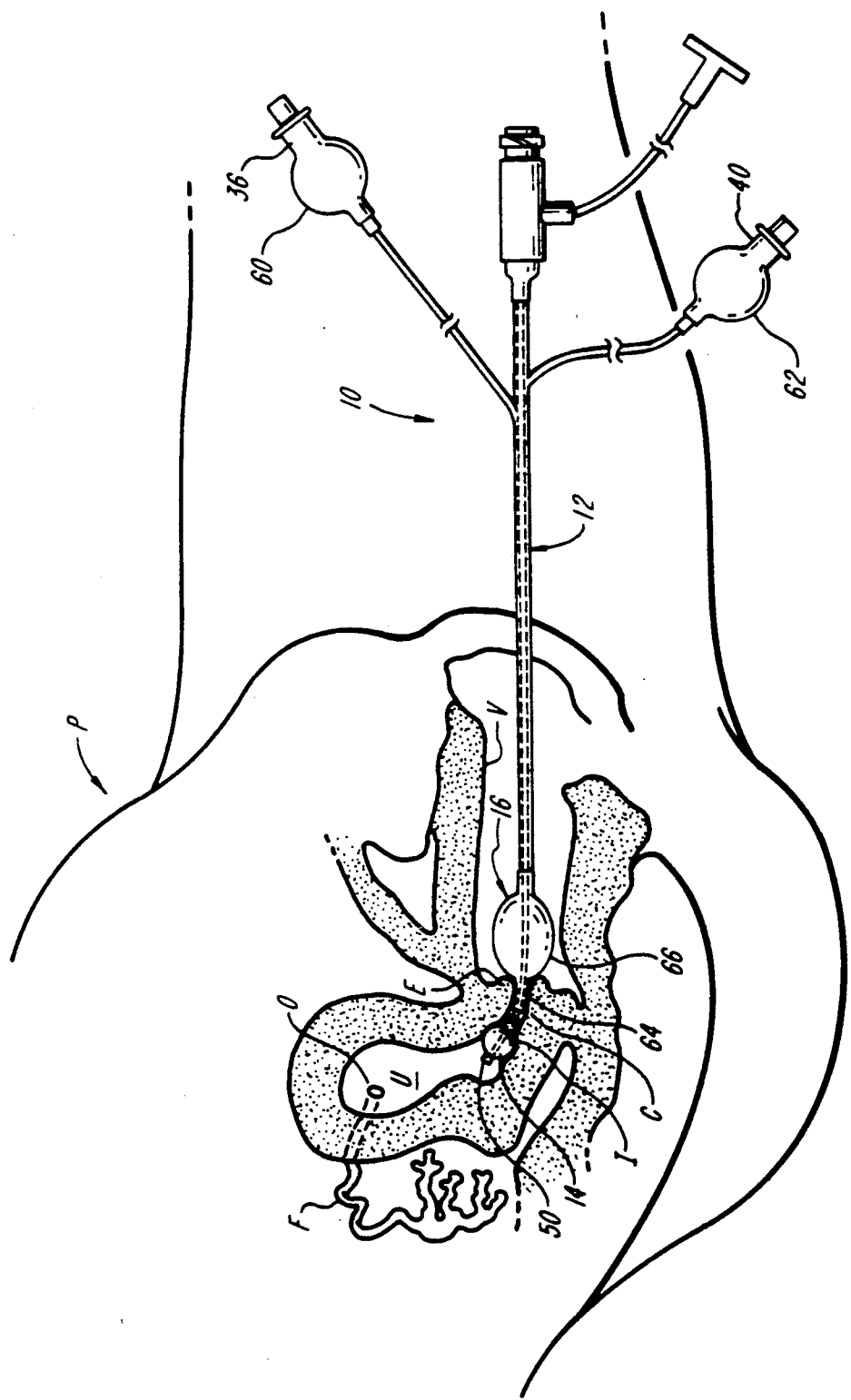
FIG. 3 is a simplified view of the uterine access device inserted within the uterus of a patient.

The operation of the uterine access device 10 according to the invention is shown in FIG. 3 in relation to a female patient P. After the vagina V is spread using a standard vaginal speculum (not shown), the distal end of the shaft 12 is inserted through the external os E of the cervix C. The distal balloon 14 is maintained in a deflated condition while it is inserted through the cervical canal and into the uterus U past the internal os I of the cervix C. The distal balloon 14 is then inflated to a diameter of 12-15 mm through the air valve 36 to 3-5 psig (155-260 mm Hg). Inflation of the distal balloon 14 is indicated to the operator by a vinyl pilot balloon 60. The pilot balloon in one construction is 1.3 inch in length, has a wall thickness of 0.040 inch, and inflates to a diameter of 0.44 inch. The proximal portion of the shaft 12 is then grasped by the operator and gently pulled proximally until resistance is met, indicating that the inflated distal balloon 14 is seated against the internal os I. The proximal balloon 16 is then inflated through the air valve 40, having a pilot balloon 62, to a pressure approximately equal to that of the distal balloon 14. The pilot balloon 62 indicates whether the proximal balloon 16 is pressurized.

Variation in length of the cervical canal is accommodated by the variable expansion along the length of the proximal balloon 16. The cervical canal is commonly 2-3 cm in length, and variations of even 1 or 2 mm can affect the quality of the seal established by standard uterine manipulative or injector devices. The uterine access device 10 according to the invention, however, automatically compensates for the variation in length because the compliant material of the balloon 16 only expands where it is not restricted by the cervical canal. Little or no dilation of the cervical canal is made by the distal portion 64, while the proximal portion 66 expands to approximately 1 inch in diameter. The distal balloon 14 and the proximal balloon 16 exert opposing forces toward each other and thereby cooperate to securely couple the device 10 to the cervix and, therefore, to the uterus U.

It is desirable for the shaft 12 to be relatively rigid when uterine manipulation is required. A central lumen communicating with the interior may not be necessary when only uterine manipulation is to be performed. When it is simply desired to introduce devices or fluids into the uterus or fallopian tubes, rigidity is not required and the shaft can be more flexible. Additionally, some or all of the proximal portion of the shaft can be curved upwardly in the same direction as the inclination of the distal portion to provide a more comfortable access angle for the operator. A proximal curvature is also useful to indicate the orientation of the distal tip 50. After insertion into the uterus, the distal tip 50 can be turned laterally to facilitate access to one of the fallopian tubes. The left fallopian tube F is shown with opening O into the uterus U.

The shaft 12 may be adjustably stiffened by removably installing a metal rod within the central lumen 32, as indicated in phantom by dashed line 52. In one construction the rod is a stainless steel rod having a diameter of 0.070 inch and carrying a luer fitting which mates with the proximal end of the device 42 to secure the rod in place. The outer diameter of the rod is small enough to allow contrast liquid or other fluid to pass alongside it within the central lumen 32. The rod may be sufficiently long and flexible to extend to the distal end 50 of shaft 12, or may extend only to the distal end of the proximal balloon 16. It is desirable for the rod to extend beyond the proximal portion 66 so that the rod lies at least partially within the cervix C.

It is preferable for the shaft 12 to define at least two ports through which fluid can be introduced into the proximal balloon 16, the ports being formed by skives to provide an opening of 0.063 inch (1.6 mm). The use of at least two longitudinally spaced ports is particularly important during deflation, when the port which lies beneath the distal portion 64 can become occluded by the balloon material before all of the fluid in the proximal portion 66 is evacuated.

While the first, distal member 14 is described above as also being an inflatable balloon, this is not a limitation of the invention. The distal member 14 can be accomplished by any device which is expandable to prevent inadvertent withdrawal of the shaft 12 from the uterus U. For example, a slitted tube which expands when compressed, referred to as a mallecot, can be used. A mallecot is found for example on the Bardex Foley catheter model no. 086, a urinary catheter available from Bard Urological Division of C. R. Bard, Inc. A pull wire then passes through the lumen 24 to activate the mallecot. An expandable member having an integral proximal portion, such as an inflatable balloon, is preferred when contrast liquid or other fluid is injected into the uterus.

From the foregoing it will be appreciated that the invention provides a self-adjusting device and technique for securely gripping a patient's cervix in a manner that provides a superior seal for HSG as well as a firm grip for uterine manipulation.

Various changes and modifications to the embodiments shown in the drawings and described above may be made within the scope of the invention. Therefore, it is intended that all matter contained in the above description and shown in the accompanying drawings shall be interpreted in an illustrative and not limiting sense.

What is claimed is:

1. A uterine access device for insertion through an adult female cervical canal having an internal os and an external os, the access device comprising:

an elongate shaft having a proximal end and a distal end;

a first, expandable distal member carried by said shaft near the distal end of said shaft;

a second, expandable proximal member being formed of a length of compliant material and being mounted on the shaft proximal to, and at a predetermined distance from, the distal member; the proximal member material having sufficient compliance so that when the proximal member is expanded with a distal portion being confined in a lumen, the confined distal portion does not substantially expand and the unconfined, more proximal portion will expand to effect a seal against the proximal end of the lumen;

whereby the spacing between the proximal and distal members and the length of the proximal member may be such that when the access device is inserted into the cervical canal and the distal member is expanded and moved against the internal os, the distal portion of the proximal member may be confined within the cervical canal and a more proximal portion of the proximal member may be disposed outside of the cervical canal so that when the proximal member is expanded, its expanded proximal portion will effect a seal against the external os while the distal member effects a seal against the internal os.

2. The device as claimed in claim 1 wherein said distal member is inflatable and encircles said shaft.

3. A device as claimed in claim 1 wherein said predetermined distance is selected in relation to the length of an adult female cervical canal such that when said distal member, when expanded distal to the cervical canal, sealingly engages the internal os of the cervix, said distal and proximal members will exert forces toward each other to seal the device within the cervical canal and block flow of fluid from the uterus along the exterior of said shaft.

4. The device as claimed in claim 1 further including means for defining a first lumen having a proximal end accessible external to the patient and a distal end communicating with said distal member.

5. The device as claimed in claim 1 further including means for defining a second lumen having a proximal end accessible external to the patient and a distal end communicating with said proximal member.

6. The device as claimed in claim 5 wherein said shaft defines at least two ports through which said second lumen communicates with said proximal member.

7. The device as claimed in claim 6 wherein one of said ports is longitudinally spaced from the other of said ports.

8. The device as claimed in claim 6 wherein one of said ports is disposed beneath the distal portion of said proximal member and another of said ports is disposed beneath the proximal portion.

9. The device as claimed in claim 1 wherein said shaft defines a first lumen communicating at a distal end with said distal member and having a proximal end accessible external to the patient, and a second lumen communicating at a distal end with said proximal member and having a proximal end accessible external to the patient, to enable actuation of said members.

10. The device as claimed in claim 9 wherein said shaft further defines a third lumen having a distal opening communicating with the uterus and having a proximal end accessible external to the patient, through which fluids or devices can be introduced into the uterus of the patient.

11. The device as claimed in claim 10 wherein said third lumen extends from the proximal end of said shaft to its distal end.

12. The device as claimed in claim 10 further including means, removably insertable into said third lumen, for selectively stiffening said shaft.

13. The device as claimed in claim 12 wherein said means for stiffening includes a metal rod insertable through the proximal end of said shaft to extend within said third lumen beyond the proximal portion of said proximal member.

14. The device as claimed in claim 1 wherein the proximal end of said shaft extends external to the patient when said distal member is expanded within the uterus.

15. The device as claimed in claim 14 wherein the proximal end of said shaft serves as a handle for manipulating the uterus.

16. The device as claimed in claim 1 wherein said proximal member is formed of latex.

17. The device as claimed in claim 16 wherein said proximal member is at least 1.5 inch in length.

18. A uterine access device comprising:
an elongate shaft having a proximal end and a distal end insertable through a cervical canal of a patient the distal end of said shaft being inclined at an angle relative to the remainder of said shaft to facilitate insertion into the uterus;
a first, expandable distal member carried by said shaft near the distal end of said shaft; and
a second, inflatable proximal member carried by a portion of said elongate shaft proximal to said distal member, said proximal member having a distal portion which lies within the cervical canal when said distal member is expanded distal to the cervical canal and having a proximal portion which expands proximal to the cervical canal, said distal and proximal members cooperating to securely couple said shaft to the uterus by automatically adjusting to the length of the cervical canal.

19. The device as claimed in claim 18 wherein said angle ranges from 15 to 25 degrees.

20. A uterine access device comprising:
an elongate shaft having a proximal end and a distal end insertable through a cervical canal of a patient;
a first, expandable distal member carried by said shaft near the distal end of said shaft; and
a second, inflatable proximal member carried by a portion of said elongate shaft proximal to said distal member, said proximal member having a distal portion which lies within the cervical canal when said distal member is expanded distal to the cervical canal and having a proximal portion which expands proximal to the cervical canal, said distal and proximal members cooperating to securely couple said shaft to the uterus by automatically adjusting to the length of the cervical canal, the distal portion of said proximal member having a wall thickness less than that of the proximal portion to preferentially induce expansion of said proximal member immediately proximal to the external os of the cervix.

21. A uterine access device comprising:
an elongate tube having a proximal end and a distal end insertable through the cervical canal of an adult human female patient, the canal having an internal os and an external os, said tube defining a central lumen through which fluids or devices can be introduced into the uterus of the patient;
an inflatable distal balloon surrounding and carried by said tube near the distal end;
a first inflation lumen extending through the tube and having a proximal end accessible external to the patient and a distal end communicating with said distal balloon;
an inflatable proximal balloon formed of a compliant material and surrounding and carried by a portion of said elongate tube proximal and at a predetermined distance from, the distal balloon, the compliance of the proximal balloon being such that when the proximal balloon is expanded with a distal portion being confined within a lumen, the confined distal portion does not substantially expand and the unconfined, more proximal portion will expand to effect a seal against the proximal end of the confining lumen and to automatically adjust to the length of the confining lumen, said distal and proximal balloons exerting forces toward each other to securely couple said tube to the confining lumen and to seal the device within the confining lumen sufficiently to block flow of fluid along the exterior of said tube; and a second inflation lumen extending through the tube and having a proximal end accessible external to the patient and a distal end communicating with said proximal balloon;

wherein the spacing between the proximal and distal balloons and the length of the proximal balloon may be such that when the device is inserted into the cervical canal of an adult human female and the distal balloon is expanded and moved against the internal os, the distal portion of the proximal balloon may be confined within the cervical canal and a more proximal portion of the proximal balloon may be disposed outside of the cervical canal so that when the proximal balloon is inflated its expanded proximal portion will effect a seal against the external os while the distal balloon effects a seal against the internal os.

22. A method of accessing a uterus in a patient, comprising:

providing a device having a shaft carrying a first, expandable distal member near a distal end of the shaft and carrying a second, inflatable proximal member disposed proximal to the distal member;

inserting the distal end of the shaft through the cervical canal to place the distal member within the uterus;

expanding the distal member to increase its diameter beyond that of the cervical canal;

withdrawing the device until the expanded distal member contacts the internal os of the cervix; and inflating the proximal member proximal to the external os of the cervix, a distal portion of the proximal member lying within and being restricted by the cervical canal, the distal and proximal members cooperating to securely couple the shaft to the uterus by automatically adjusting to the length of the cervical canal.

23. A method of accessing a uterus in a patient, comprising:

providing a device having an elongate tube carrying a distal inflatable member near a distal end of the tube and carrying a proximal inflatable member formed of a compliant material;

inserting the distal end of the tube through the cervical canal to place the distal member within the uterus;

inflating the distal member to increase its diameter beyond that of the cervical canal;

gently withdrawing the device until the inflated distal member contacts the internal os of the cervix; and inflating the proximal member proximal to the external os of the cervix, a distal portion of the proximal member lying within and being restricted by the cervical canal, the distal and proximal members cooperating to securely couple the shaft to the uterus and to seal the device within the cervical canal to block flow of fluid from the uterus along the exterior of the tube.

* * * * *